US012636417B2

(12) United States Patent
Micallef

(10) Patent No.: US 12,636,417 B2
(45) Date of Patent: May 26, 2026

(54) DEVICE FOR INLINE MONITORING OF FREE NUCLEOSOMES IN BLOOD

(71) Applicant: Belgian Volition SRL (BE/BE), Isnes (BE)

(72) Inventor: Jacob Vincent Micallef, London (GB)

(73) Assignee: Belgian Volition SRL, Isnes (BE)

( * ) Notice: Subject to any disclaimer, the term of this patent is extended or adjusted under 35 U.S.C. 154(b) by 472 days.

(21) Appl. No.: 18/246,016

(22) PCT Filed: Sep. 21, 2021

(86) PCT No.: PCT/EP2021/075877
§ 371 (c)(1),
(2) Date: Mar. 20, 2023

(87) PCT Pub. No.: WO2022/058604
PCT Pub. Date: Mar. 24, 2022

(65) Prior Publication Data
US 2023/0355851 A1 Nov. 9, 2023

(30) Foreign Application Priority Data

| Sep. 21, 2020 | (GB) | ....................................... 2014864 |
| Nov. 30, 2020 | (GB) | ....................................... 2018837 |
| Jan. 20, 2021 | (GB) | ....................................... 2100770 |

(51) Int. Cl.
A61M 1/34 (2006.01)
(52) U.S. Cl.
CPC ................................. A61M 1/3496 (2013.01)
(58) Field of Classification Search
CPC .................................................. A61M 1/3496

USPC ......................................................... 604/6.01
See application file for complete search history.

(56) References Cited

U.S. PATENT DOCUMENTS

| 9,364,601 | B2 * | 6/2016 | Ichim ........................ A61M 1/16 |
| 2007/0092509 | A1 * | 4/2007 | Mittra ................. A61M 1/3695 |
| | | | 424/140.1 |
| 2014/0206015 | A1 | 7/2014 | Micallef |
| 2016/0061824 | A1 * | 3/2016 | Hahn ................. G01N 33/5308 |
| | | | 436/501 |

FOREIGN PATENT DOCUMENTS

| EP | 2775304 A1 | 9/2014 |
| WO | WO 2005/019826 A1 | 3/2005 |
| WO | WO 2012/172345 A2 | 12/2012 |
| WO | WO 2013/030578 A2 | 3/2013 |

(Continued)

OTHER PUBLICATIONS

Ashar et al., "The Role of Extracellular Histones in Influenza Virus Pathogenesis", Am J. Pathol., vol. 188, No. 1, pp. 135-148 (2018).

(Continued)

*Primary Examiner* — Andrew J Mensh
(74) *Attorney, Agent, or Firm* — McDermott Will & Schulte LLP; Brennen P. Baylor; Judy M. Mohr

(57) ABSTRACT

The present invention relates to an extracorporeal device or an ex vivo organ perfusion device comprising an inline monitoring method or device for measuring cell free nucleosomes, particularly an apheresis device comprising a monitoring method or device for measuring cell free nucleosomes in the blood of a subject.

18 Claims, 5 Drawing Sheets

(56)                    References Cited

FOREIGN PATENT DOCUMENTS

| | | |
|---|---|---|
| WO | WO 2013/030579 A1 | 3/2013 |
| WO | WO 2013/084002 A2 | 6/2013 |
| WO | WO 2017/049279 A1 | 3/2017 |
| WO | WO 2017/185086 A1 | 10/2017 |
| WO | WO 2019/053243 A1 | 3/2019 |
| WO | WO 2019/169263 A1 | 9/2019 |
| WO | WO 2021/063708 | 4/2021 |
| WO | WO 2022/058604 A1 | 3/2022 |

OTHER PUBLICATIONS

Barbosa and Reis, "A critical insight into the development pipeline of microfluidic immunoassay devices for the sensitive quantitation of protein biomarkers at the point of care", Analyst, vol. 142, No. 6, pp. 858-882 (2017).

Caldarone et al., "Neutrophil extracellular traps in ex vivo lung perfusion perfusate. Predict the clinical outcome of lung transplant recipients", Eur. Respir. J., vol. 53, No. 1801736 5 pages (2019) Online article downloaded from https://erj.ersjournals.com/content/erj/53/4/1801736.full.pdf (2019).

Cavalier et al., "Circulating Nucleosomes as Potential Markers to Monitor COVID-19 Disease Progression", Front. Mol. Biosci., vol. 8, Art. 600881, 9 pages (2021).

Danthi, "Viruses and the Diversity of Cell Death", Annu. Rev. Virol., vol. 3, pp. 533-553 (2016).

De Back et al., "Therapeutic plasma apheresis: Expertise and indications", Transfus. Apher. Sci., vol. 58, No. 3, pp. 254-257 (2019).

Fischer et al., "Diagnostic leukapheresis enables reliable detection of circulating tumor cells of nonmetastatic cancer patients", PNAS, vol. 110, No. 41, pp. 16580-16585 (2013).

Hoeksema et al. "Histones as mediators of host defense, inflammation and thrombosis", Future Microbiol., vol. 11, No. 3, pp. 441-453 (2016).

Honore et al., "Cytokine removal in human septic shock: Where are we and where are we going?", Ann. Intensive Care, vol. 9, No. 1, Art. 56, 13 pages (2019).

International Search Report from International Application No. PCT/EP2021/075877, 5 pages, Mailed Feb. 8, 2022, application now published as WO2022/058604 on Mar. 24, 2022.

Israni et al., "OPTN/SRTR 2018 Annual Data Report: Deceased Organ Donation", Am J Transplant., vol. 20, Suppl. 1, pp. 509-541 (2019).

Kalaaji et al., "Glomerular apoptotic nucleosomes are central target structures for nephritogenic antibodies in human SLE nephritis", Kidney Int., vol. 71, No. 7, pp. 664-672 (2007).

Koczula and Gallotta, "Lateral flow assays", Essays Biochem., vol. 60, No. 1, pp. 111-120 (2016).

Kusaoi et al., "Separation of Circulating MicroRNAs Using Apheresis in Patients With Systemic Lupus Erythematosus", Ther. Apher. Dial., vol. 20, No. 4, pp. 348-353 (2016).

Mehrotra, "Biosensors and their applications—A review", J. Oral Biol. Craniofac. Res., vol. 6, No. 2, pp. 153-159 (2016).

Neubert et al., "Interplay of Na+ Balance and Immunobiology of Dendritic Cells", Frontiers in Immunology, vol. 10, Art. 599, 6 pages (2019).

Rea et al., "Circulating Nucleosome Immunoassay: Evaluating a Clinically-applicable Test to Risk Stratify COVID-19 and Target Anticoagulation", ISTH Academy., Abstract #PB0268, 1 page (2021).

Sollberger et al., "Neutrophil Extracellular Traps: The Biology of Chromatin Externalization", Dev. Cell, vol. 44, No. 5, pp. 542-553 (2018).

Stanford et al., "Identifying tools to track hypercoagulability in COVID-19 patients. Exploring Global Haemostasis (ROTEM) and Neutrophil Extracellular Traps (NETs) immunoassays", ISTH Academy., Abstract #PB0152, 2 pages (2021).

Thalin et al., "Neutrophil Extracellular Traps: Villains and Targets in Arterial, Venous, and Cancer-Associated Thrombosis", Arterioscler. Thromb. Vasc. Biol., vol. 39, No. 9, pp. 1724-1738 (2019).

Urban et al., "Neutrophil extracellular traps contain calprotectin, a cytosolic protein complex involved in host defense against Candida albicans", PLOS Pathog., vol. 5, No. 10, Art. e1000639 18 pages (2009).

Wang et al., "Histone hypercitrullination mediates chromatin decondensation and neutrophil extracellular trap formation", J. Cell Biol., vol. 184, No. 2, pp. 205-213 (2009).

Ward, "Conventional Apheresis Therapies: A Review", J. Clin. Apher., vol. 26, No. 5, pp. 230-238 (2011).

Braun et al., "Limitation of Circulating cfDNA Under the Use of a Cytokine Elimination Adsorber (CytoSorb) in Cardiac Surgery", The Thoracic and Cardiovascular Surgeon Reports, vol. 66, pp. S1-S110, Feb. 18, 2018, Short Presentation Full Text, 1-page, online article obtained from https://www.thieme-connect.com/products/ejournals/html/10.1055/s-0038-1628092 (2018).

Gocho et al., "Removal of circulating neutrophil extracellular trap components with an immobilized polymyxin B filter: A preliminary study", Shock, vol. 54, No. 1, pp. 44-49 (2020).

Kanou et al., "Cell-free DNA in human ex vivo lung perfusate as a potential biomarker to predict the risk of primary graft dysfunction in lung transplantation", The Journal of Thoracic and Cardiovascular Surgery, vol. 162, No. 2, pp. 490-499 (2021).

* cited by examiner

(a)  H3.1-nucleosome level in samples taken from pig (ng/ml)

(b)  H3.1-nucleosome level in plasma entering cartridge (ng/ml)

(c) H3.1-nucleosome level in plasma leaving cartridge (ng/ml)

FIGURE 3 (contd.)

H3.1-nucleosomes (ng/ml)

DEVICE FOR INLINE MONITORING OF FREE NUCLEOSOMES IN BLOOD

CROSS-REFERENCE TO RELATED APPLICATIONS

This application is a U.S. National Stage Application under 35 U.S.C. § 371 which claims the benefit of priority to International Patent Application No. PCT/EP2021/075877, filed Sep. 21, 2021, which claims the benefit of priority to GB Patent Application No. 2100770.3, filed Jan. 20, 2021, GB Patent Application No. 2018837.1, filed Nov. 30, 2020, and GB Patent Application No. 2014864.9, filed Sep. 21, 2020, each of which is hereby incorporated by reference in its entirety.

FIELD OF THE INVENTION

The present invention relates to an inline monitoring device for measuring cell free nucleosomes, particularly for use in apheresis devices.

BACKGROUND OF THE INVENTION

Many diseases involve a pathology in which the blood of a subject contains an abnormal or pathogenic blood constituent which threatens the health or even the life of the subject. The toxic moiety may be absent from the circulation of healthy persons but present in diseased subjects (e.g. a monoclonal IgG or IgM paraproteins in multiple myeloma patients) or may be present in both healthy and diseased subjects but at an elevated level in diseased subjects (e.g. platelets, cytokine molecules and nucleosomes). The toxic moiety may be any of a variety of types including without limitation a cell, a platelet, a small molecule or a large molecule (for example a protein, lipoprotein or nucleoprotein). Apheresis is an extracorporeal method of treating such diseases where the blood is removed from the subject and toxic moieties are removed before the blood before it is returned to the subject.

One form of apheresis is whole blood apheresis. Another form of apheresis is plasmapheresis which involves the removal of whole blood from a subject into an extracorporeal instrument, separation of abnormal plasma from the whole blood, discarding the abnormal plasma and returning the remaining whole blood to the subject or, alternatively, the removal of abnormal substances from the plasma before the plasma is rejoined with the whole blood and returned to the subject. Solid phase adsorbents that bind to abnormal substances in the plasma may be used to remove such plasma components in extra corporeal plasmapheresis before the plasma is rejoined with the whole blood and returned to the subject. Kidney dialysis for the removal of physiological waste products from the circulation is a common form of apheresis.

Sepsis is a life-threatening inflammatory disease triggered by a bacterial, fungal, viral or protozoan infection and characterised by a cytokine storm with elevated levels of circulating cytokines as well as elevated production of neutrophil extracellular traps (NETs) and elevated levels of circulating nucleosomes. Elevated cytokine and NETs production by NETosis is pathological and has been found to lead to thrombosis, low blood pressure, high blood lactate and low urine output, leading eventually to respiratory distress, loss of consciousness and multiple organ failure. Sepsis requires immediate treatment with intravenous fluids and antimicrobials often in an intensive care setting.

Mechanical ventilation and dialysis may be needed to support the function of the lungs and kidneys, as well as preventive measures for thrombosis. The risk of death from severe sepsis may be 50% and is a leading cause of death worldwide.

Immediate treatment of sepsis to reduce circulating cytokine levels may also be affected by removal of cytokines including interleukin-6 (IL-6) and tumour necrosis factor (TNF-α) from the circulation by plasmapheresis using a solid phase adsorbent contained in a cartridge through which the subject's separated plasma is passed before being returned with the whole blood to the body (Honore et al. (2019) Ann. Intensive Care 9: 56). Another adsorbent has been described for the removal of elevated levels of cell free DNA (cfDNA) or NETs and circulating NETs degradation material from the plasma of subjects with sepsis. In this technology histone H1.3 is used as a binder of cfDNA or NETs in plasmapheresis (WO2019053243). H1.3 cannot be used as an adsorbent for NETs or cfDNA in whole blood apheresis as H1 is disruptive to cell membranes.

One limitation with these devices is that current monitoring of the treatment is poor. The progress of the treatment over time, or lack thereof, is not monitored. In particular, there are no methods currently for the monitoring of cfDNA or NETs levels for use in extracorporeal blood treatments, including when the treatment is designed to remove cfDNA or NETs. This leads to disadvantages such as, (i) the efficacy of the treatment is unknown and may be continued when other treatments would be preferable, (ii) the length of time required to reach a threshold depletion of the pathologic substance is unknown so the treatment may be continued when no longer required, (iii) the treatment may be terminated too early for the same reason or (iv) the real time saturation level of the adsorbent material for the pathologic substance during treatment is unknown such that the treatment may be continued with reduced effectiveness when the column is saturated. Therefore, there remains a need in the art to provide a method of monitoring progression of apheresis to help improve patient safety and treatment efficiency.

Extracorporeal blood treatments include a large variety of apheresis types including for example, without limitation, to remove physiological waste products, to collect stem cells for autologous transplantation, to collect white blood cells (for example, in CAR T cell therapy), to exchange red blood cells (for example, in the treatment of sickle cell disease), to exchange plasma and to oxygenate the blood (as in extracorporeal membrane oxygenation or ECMO).

Extracorporeal blood treatments are known to cause of inflammation and may themselves lead to the generation of elevated levels of NETs. Therefore, monitoring the level of circulating NETs or cfDNA is useful in all such treatments to improve patient safety and treatment efficiency.

SUMMARY OF THE INVENTION

According to a first aspect of the invention, there is provided an extracorporeal device comprising a monitoring method or device for measuring the level of cell free nucleosomes present in the blood of a subject.

According to a further aspect, there is provided an extracorporeal method for the treatment of the blood of a subject comprising a monitoring method or inline device for measuring the level of cell free nucleosomes or NETs present in the blood of the subject.

According to a yet further aspect, there is provided a device for the extracorporeal treatment of the blood of a subject comprising a monitoring method or inline device for measuring the level of cell free nucleosomes or NETs present in the blood of the subject.

According to a still further aspect, there is provided an apheresis device comprising one or more affinity matrices for removing one or more pathogenic substances from the blood of a subject that includes an inline monitoring method or device for measuring the level of cell free nucleosomes present in the blood of the subject.

According to a further aspect, there is provided a method of monitoring a subject during an extracorporeal procedure comprising: passing the blood of the subject through the extracorporeal device described herein; and monitoring the level of cell free nucleosomes in the blood of the subject using the monitoring method or device of the extracorporeal device.

According to a yet further aspect, there is provided a method of treating a disease in a subject in need thereof comprising: passing the blood of the subject through the extracorporeal device described herein; and monitoring the level of cell free nucleosomes in the blood of the subject using the monitoring method or device of the extracorporeal device.

According to another aspect of the invention, there is provided an ex vivo organ perfusion method or device comprising a monitoring method or device for measuring the level of cell free nucleosomes present in the liquid perfusate.

DETAILED DESCRIPTION

Figure 1:
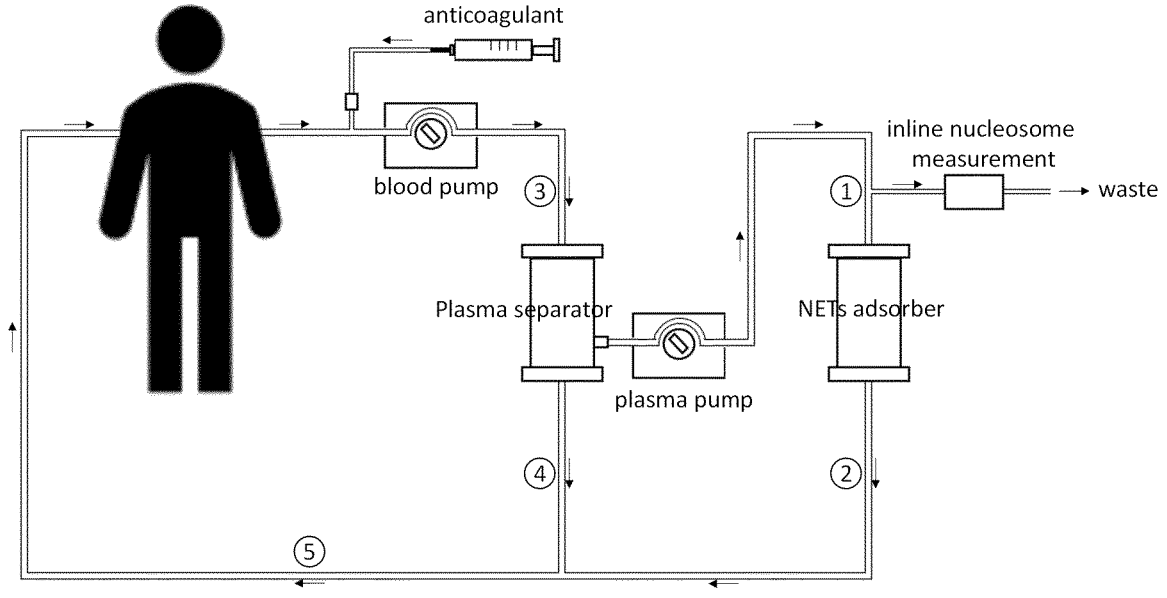
FIG. 1. Simplified cartoon representation of a plasmapheresis arrangement to remove NETs from the blood of a subject including inline measurement of nucleosomes. Blood is pumped from the body with addition of an anticoagulant into a plasma separator. Separated plasma is pumped into a solid phase nucleosome/NETs adsorption matrix. Plasma which has been depleted of NETs/nucleosomes is returned to the body along with the rest of the subject's blood. In the cartoon inline nucleosome measurement is performed in plasma prior to nucleosome adsorption at position 1. Plasma nucleosome measurement may also be made at position 2. Plasma nucleosome measurement may also be made at both positions 1 and 2 to provide information on both the current circulating nucleosome levels in the subject as well as to monitor the effectiveness of nucleosome/NETs depletion of the NETs adsorber. Whole blood nucleosome measurement may also be made at positions 3, 4 or 5.

Extracorporeal treatments may involve a variety of treatments which require monitoring of NETs levels or cfDNA levels to ensure patient safety and optimal therapeutic outcomes. Therefore, according to a first aspect of the invention, there is provided an extracorporeal device comprising a monitoring method or device for measuring the level of cell free nucleosomes or NETs present in the circulation of the subject and/or in the blood, or blood plasma of the subject, circulating extracorporeally.

Apheresis is an extracorporeal treatment that removes pathogenic substances or components in the blood from a patient to treat disease (e.g. Ward M. D., (2011) Conventional Apheresis Therapies: A Review Journal of Clinical Apheresis 26:230-238). Therefore, references herein to "apheresis device" refer to a device for modifying the composition of blood ex vivo before returning the blood to the subject.

Methods of the current art focus on the apheresis treatment method, however it is important to consider monitoring the progression of the treatment to ensure that the patient receives sufficient treatment and improve overall efficiency of the procedure. This is especially important as the demand for apheresis grows; the increased burden on apheresis resources can be minimised by ensuring that apheresis is only performed on the patient for as long as necessary.

According to one aspect, there is provided an apheresis device comprising one or more affinity matrices for removing one or more pathogenic substances from the blood of a subject and an inline monitoring device for measuring the level of cell free nucleosomes present in the blood of the subject. Therefore, in one embodiment there is provided an extracorporeal device further comprising one or more affinity matrices for removing one or more pathogenic substances from the blood of the subject.

In particular, the pathogenic substances are cell free DNA (cfDNA) and/or neutrophil extracellular traps (NETs). Measuring the level of cell free nucleosomes can be used to monitor the progression of treatment and determine when the level of pathogenic substance, particularly NETs, has reached an acceptable level so that apheresis may be stopped.

Monitoring Method or Device

In one embodiment, the monitoring method or device measures the level of cell free nucleosomes present in the blood of the subject in real time. In some embodiments, the monitoring device is an inline monitoring device. In one aspect of the invention, discreet measurements of plasma or whole blood nucleosome levels are made at intervals, for example at 15 minute intervals or 30 or 60 minute intervals. In one embodiment, the monitoring method or device is a disposable or reusable measurement device. It may be plugged into the extracorporeal device, such as the apheresis device, for measurement. Therefore, measurement may be performed inline using any device fitted to receive blood or plasma from the subject.

In one embodiment measurement is performed using a lateral flow immunoassay cartridge or device that measures nucleosome levels rapidly (for example in 5 minutes or in 10, 15 or 20 minutes). In this embodiment the lateral flow device may be similar in design to that of a common lateral flow test as used, for example, in urine pregnancy tests or other home use tests involving the testing of a finger-prick of blood. Such tests are well described in the art (for example by Koczula and Gallotta, Essays in Biochemistry (2016) 60: 111-120).

In another embodiment, measurement is performed using a microfluidic immunoassay device. Microfluidic immunoassay devices are miniaturised biomarker immunoassays and also well known in the art. Microfluidic devices have a number of advantages over lateral flow tests including greater analytical quantitative accuracy, simplified fluidics, a reduced amount of reagents and shorter assay times which are often 5 minutes or less (see Barbosa and Reis, Analyst (2017) 142: 858). Microfluidic devices have been produced that target many protein biomarkers including cardiac biomarkers (e.g. troponin I, troponin T, creatine kinase and myoglobin), cancer biomarkers (e.g. prostate specific antigen, carcinoma embryonic antigen, $\alpha$-fetaprotein and cancer antigen 125) and inflammatory biomarkers (e.g. C-reactive protein, TNF-$\alpha$, IL-1, IL-4 and IL-6).

An accurate, reusable microfluidic device for the rapid measurement of insulin within 30 seconds of sampling has been reported (Cohen et al. Microchim. Acta (2017) 184: 835-841). This device utilises an anti-insulin antibody coated polystyrene microspheres in a microfluidic device to provide insulin measurements in approximately 30 seconds which can be repeated as frequently as desired using a pool of reagents to provide near real time measurement of insulin. Therefore, in one embodiment of the invention there is provided a rapid, real time measurement of nucleosomes (and optionally other inflammatory markers) by means of a microfluidic device, such as an inline microfluidic device.

In a further embodiment of the invention a biosensor device (e.g. an inline biosensor device) is used to detect the level (or concentration) of nucleosomes. A biosensor is an analytical device that convert a biological response into an electrical signal. Typically a biosensor for use as a monitor of nucleosome levels in an apheresis or plasmapheresis instrument, will consist of a sensing component that recognizes the analyte nucleosomes (for example a specific binder of nucleosomes such as an antibody or a chromatin protein such as histone H1 immobilised on a solid phase) that produces a signal and a signal transducer to provide an electrical output. This can be used in a repeat discrete measurement mode or in a continuous mode where the marginal binding of nucleosomes is measured in a moving time frame to provide real time electrical signal monitoring. In one embodiment, DNA is detected using a biosensor as nucleic acid-based sensing systems are more sensitive than antibody-based detection methods. In one embodiment the invention utilises a DNA sensing component that detects DNA by means of binding to DNA intercalating moieties. Biosensors are well described in the art, for example by Mehrotra J. Oral Biol. Craniofac. Res. (2016) 6(2): 153-9.

In one embodiment, the inline monitoring device comprises a solid phase with immobilized binding agents for binding cell free nucleosomes. In a further embodiment, the monitoring method or device comprises a solid phase with immobilized binding agents for binding cell free nucleosomes.

Nucleosomes are released into circulation on fragmentation of chromatin on cell death. Many infections, such as viral infections, initiate cell death through a variety of mechanisms (cell binding and entry, endosomal TLR3 activation and gene expression) thereby increasing the number of circulating nucleosomes in the blood (Danthi et al., Annu. Rev. Virol. (2016) 3: 533-53). In addition, infections can induce NETosis whereby post-translational histone modifications, such as hypercitrullination of histones H3 and H4 (Wang Y et al., J. Cell Biol. (2009) 184(2): 205-213), promote decondensation of chromatin which is released into circulation together as a first line response to infection. However, extracellular nucleosomes and NETs can cause severe complications if not cleared rapidly. For example, nucleosome binding to the glomerular membrane is associated with kidney damage in lupus (Kalaaji et al., Kidney Int. (2007) 71(7): 665-672), whilst NETs have been shown to intensify pulmonary injury during viral pneumonia (Ashar et al., Am. J. Pathol. (2018) 188(1): 135-148). Indeed, host directed NET toxicity is associated with respiratory distress, occlusion of narrow airways, epithelial cell damage, inflammatory response and thrombus formation (Marcos et al., Nat. Med. (2010) 16: 1018-23; Hoeksema et al., Future Microbiol. (2016) 11: 441-53).

The nucleosome is the basic unit of chromatin structure and consists of a protein complex of eight highly conserved core histones (comprising of a pair of each of the histones H2A, H2B, H3, and H4). Around this complex is wrapped approximately 146 base pairs of DNA. Another histone, H1 or H5, acts as a linker and is involved in chromatin compaction. The DNA is wound around consecutive nucleosomes in a structure often said to resemble "beads on a string" and this forms the basic structure of open or euchromatin. In compacted or heterochromatin this string is coiled and super coiled into a closed and complex structure (Herranz and Esteller, Methods Mol. Biol. (2007) 361: 25-62).

References to "nucleosome" may refer to "cell free nucleosome" when detected in body fluid samples. It will be appreciated that the term cell free nucleosome throughout this document is intended to include any cell free chromatin fragment that includes one or more nucleosomes.

It will be understood that the cell free nucleosome may be detected by binding to a component thereof. The term "component thereof" as used herein may refer to a part of the nucleosome, i.e. the whole nucleosome does not need to be detected. The component of the cell free nucleosomes may be selected from the group consisting of: a histone protein (i.e. histone H1, H2A, H2B, H3 or H4), a histone post-translational modification, a histone variant or isoform, a protein bound to the nucleosome (i.e. a nucleosome-protein adduct), a DNA fragment associated with the nucleosome and/or a modified nucleotide associated with the nucleosome. For example, the component thereof may be histone (isoform) H3.1 or histone H1 or DNA.

The monitoring method or device, such as the inline monitoring device, of the invention may measure the level of (cell free) nucleosomes per se. References to "nucleosomes per se" refers to the total nucleosome level or concentration present in the sample, regardless of any epigenetic features the nucleosomes may or may not include. Thus, in one embodiment, the binding agent binds to a feature of a core nucleosome that is common to all or most nucleosomes. Detection of the total nucleosome level typically involves detecting a histone protein common to all nucleosomes, such as histone H4. Therefore, nucleosomes per se may be measured by detecting a core histone protein, such as histone H4. As described herein, histone proteins form structural units known as nucleosomes which are used to package DNA in eukaryotic cells.

The cell free nucleosome may be mononucleosomes, oligonucleosomes, a constituent part of a larger chromatin fragment or a constituent part of a NET or a mixture thereof.

Mononucleosomes and oligonucleosomes have been detected by Enzyme-Linked ImmunoSorbant Assay (ELISA) and several methods have been reported (e.g. Salgame et al. Nucleic Acids Research, 25(3), 680-681 (1997); Holdenrieder et al. Int. J. Cancer 95, 114-120 (2001); van Nieuwenhuijze et al. Ann Rheum Dis; 62: 10-14 (2003)). These assays typically employ an anti-histone antibody (for example anti-H2B, anti-H3 or anti-H1, H2A, H2B, H3 and H4) as capture antibody and an anti-DNA or anti-H2A-H2B-DNA complex antibody as detection antibody.

Circulating nucleosomes are not a homogeneous group of protein-nucleic acid complexes. Rather, they are a heterogeneous group of chromatin fragments originating from the digestion of chromatin on cell death and include an immense variety of epigenetic structures including particular histone isoforms (or variants), post-translational histone modifications, nucleotides or modified nucleotides, and protein adducts. In one embodiment, the binding agent binds to an epigenetic feature of cell free nucleosomes. It will be clear to those skilled in the art that an elevation in nucleosome levels will be associated with elevations in some circulating nucleosome subsets containing particular epigenetic signals including nucleosomes comprising particular histone isoforms (or variants), comprising particular post-translational histone modifications, comprising particular nucleotides or modified nucleotides and comprising particular protein adducts. Assays for these types of chromatin fragments are known in the art (for example, see WO2005/019826, WO2013/030579, WO2013/030578, WO2013/084002 which are herein incorporated by reference).

The monitoring method or device, such as the inline monitoring device, may measure the level of cell free nucleosomes per se and/or an epigenetic feature of a cell free nucleosome. It will be understood that the terms "epigenetic signal structure" and "epigenetic feature" are used interchangeably herein. They refer to particular features of the nucleosome that may be detected. In one embodiment, the epigenetic feature of the nucleosome is selected from the group consisting of: a post-translational histone modification, a histone isoform, a modified nucleotide and/or proteins bound to a nucleosome in a nucleosome-protein adduct.

In one embodiment, the epigenetic feature of the nucleosome comprises one or more histone variants or isoforms. The epigenetic feature of the cell free nucleosome may be a histone isoform, such as a histone isoform of a core nucleosome, in particular a histone H3 isoform. The term "histone variant" and "histone isoform" may be used interchangeably herein. The structure of the nucleosome can also vary by the inclusion of alternative histone isoforms or variants which are different gene or splice products and have different amino acid sequences. Many histone isoforms are known in the art. Histone variants can be classed into a number of families which are subdivided into individual types. The nucleotide sequences of a large number of histone variants are known and publicly available for example in the National Human Genome Research Institute NHGRI Histone Database (Mariño-Ramirez et al. The Histone Database: an integrated resource for histones and histone fold-containing proteins. *Database* Vol. 2011 and http://genome.nhgri.nih.gov/histones/complete.shtml), the GenBank (NIH genetic sequence) Database, the EMBL Nucleotide Sequence Database and the DNA Data Bank of Japan (DDBJ). For example, variants of histone H2 include H2A1, H2A2, mH2A1, mH2A2, H2AX and H2AZ. In another example, histone isoforms of H3 include H3.1, H3.2 and H3t. In one embodiment, the histone isoform is H3.1.

The structure of nucleosomes can vary by post translational modification (PTM) of histone proteins. PTM of histone proteins typically occurs on the tails of the core histones and common modifications include acetylation, methylation or ubiquitination of lysine residues as well as methylation of arginine residues and phosphorylation of serine residues and many others. Many histone modifications are known in the art and the number is increasing as new modifications are identified (Zhao and Garcia (2015) Cold Spring Harb Perspect Biol, 7: a025064). Therefore, in one embodiment, the epigenetic feature of the cell free nucleosome may be a histone post translational modification (PTM). The histone PTM may be a histone PTM of a core nucleosome, e.g. H3, H2A, H2B or H4, in particular H3, H2A or H2B. In particular, the histone PTM is a histone H3 PTM. Examples of such PTMs are described in WO 2005/019826.

For example, the post translational modification may include acetylation, methylation, which may be mono-, di- or tri-methylation, phosphorylation, ribosylation, citrullination, ubiquitination, hydroxylation, glycosylation, nitrosylation, glutamination and/or isomerisation (see Ausio (2001) Biochem Cell Bio 79: 693). In one embodiment, the histone PTM is selected from citrullination or ribosylation. In a further embodiment, the histone PTM is H3 citrulline (H3cit) or H4 citrulline (H4cit). In a yet further embodiment, the histone PTM is H3cit, such as H3R8cit.

In one embodiment, the histone PTM is ribosylation, also referred to as ADP-ribosylation. Post-translational histone ADP-ribosylation of nucleosomes occupying promoters of inflammatory response markers in macrophages is stimulated by exposure to lipopolysaccharides leading to elevated transcription and may have antiviral properties.

A group or class of related histone post translational modifications (rather than a single modification) may also be detected. A typical example, without limitation, would involve a 2-site immunoassay employing one antibody or other selective binder directed to bind to nucleosomes and one antibody or other selective binder directed to bind the group of histone modifications in question. Examples of such antibodies directed to bind to a group of histone modifications would include, for illustrative purposes without limitation, anti-pan-acetylation antibodies (e.g. a Pan-acetyl H4 antibody [H4panAc]), anti-citrullination antibodies or anti-ubiquitin antibodies.

In one embodiment, the epigenetic feature of the nucleosome comprises one or more DNA modifications. In addition to the epigenetic signalling mediated by nucleosome histone isoform and PTM composition, nucleosomes also differ in their nucleotide and modified nucleotide composition. Some nucleosomes may comprise more 5-methylcytosine residues (or 5-hydroxymethylcytosine residues or other nucleotides or modified nucleotides) than other nucleosomes. In one embodiment, the DNA modification is selected from 5-methylcytosine or 5-hydroxymethylcytosine.

In one embodiment, the epigenetic feature of the nucleosome comprises one or more protein-nucleosome adducts or complexes. A further type of circulating nucleosome subset is nucleosome protein adducts. It has been known for many years that chromatin comprises a large number of non-histone proteins bound to its constituent DNA and/or histones. These chromatin associated proteins are of a wide variety of types and have a variety of functions including transcription factors, transcription enhancement factors, transcription repression factors, histone modifying enzymes, DNA damage repair proteins and many more. These chromatin fragments including nucleosomes and other non-histone chromatin proteins or DNA and other non-histone chromatin proteins are described in the art.

In one embodiment, the protein adducted to the nucleosome (and which therefore may be used as a biomarker) is selected from: a transcription factor, a High Mobility Group Protein or chromatin modifying enzyme. References to "transcription factor" refer to proteins that bind to DNA and regulate gene expression by promoting (i.e. activators) or suppressing (i.e. repressors) transcription. Transcription factors contain one or more DNA-binding domains (DBDs), which attach to specific sequences of DNA adjacent to the genes that they regulate. All of the circulating nucleosomes and nucleosome moieties, types or subgroups described herein may be useful in the present invention.

A number of proteins occur in NETs that are adducted directly or indirectly to nucleosomes. These proteins include, without limitation, myeloperoxidase (MPO), neutrophil elastase (NE), lactotransferrin, azurocidin, cathepsin G, leukocyte proteinase 3, lysozyme C, neutrophil defensin 1, neutrophil defensin 3, myeloid cell nuclear differentiation antigen, S100 calcium-binding protein A8, S100 calcium-binding protein A9, S100 calcium-binding protein A12, actin β, actin γ, alpha-actin, plastin-2, cytokeratin-10, catalase, alpha-enolase and transketolase (Urban et al., PLOS Pathogens. (2009) 10: e1000639). Any nucleosome-protein adduct that occurs in NETs is a useful adduct for the detection of elevated levels of NETs in methods of the invention. C-reactive protein (CRP) may also be adducted to nucleosomes in NETs and nucleosome-CRP adduct is therefore a useful adduct for the detection of elevated levels of NETs in methods of the invention.

In preferred embodiments the protein adduct associated with a cell free nucleosome detected is an MPO-nucleosome adduct or a NE-nucleosome adduct.

The term "biomarker" means a distinctive biological or biologically derived indicator of a process, event, or condition. Biomarkers can be used in methods of diagnosis, e.g. clinical screening, and prognosis assessment and in monitoring the results of therapy, identifying patients most likely to respond to a particular therapeutic treatment, drug screening and development.

Methods and uses described herein are tested in body fluid samples, in particular blood, serum or plasma samples taken from the blood passing through the apheresis device. Preferably, plasma samples are used.

The subject may be, for example, a human subject or a (non-human) animal subject. References to "subject" or "patient" are used interchangeably herein. In one embodiment, the subject is a human. In one embodiment, the subject is a (non-human) animal.

Additional Biomarkers

In one embodiment, the monitoring method or device, such as the inline monitoring device, comprises a panel of markers to be measured in the blood of the subject.

Therefore, the level of cell free nucleosomes may be detected or measured as one of a panel of measurements. The panel may comprise different epigenetic features of the nucleosome as described hereinbefore (e.g. a histone isoform and a PTM). Biomarkers useful in a panel test for the detection of infections that require medical intervention include, without limitation, cytokine moieties (particularly interleukins), C-reactive protein, myeloperoxidase, D-Dimer, factor VII-activating protease (FSAP), fibrinogen and fibrin/fibrinogen breakdown products. In one embodiment, the panel comprises one or more cytokines, such as one or more interleukins.

Interleukins (ILs) are a group of cytokines, usually secreted by leukocytes, that act as signal molecules. They have key roles in stimulating immune responses and inflammation. They were first identified in the 1970s and have been designated numerically as more interleukin types have been discovered. Examples of interleukins include, but are not limited to: IL-1, IL-2, IL-3, IL-4, IL-5, IL-6, IL-7, IL-8, IL-9, IL-10, IL-11, IL-12, IL-13, IL-14 and IL-15.

In one embodiment, the one or more interleukins is selected from the group consisting of: Interleukin-6 (IL-6) and Interleukin-12 (IL-12).

The interleukin may be IL-6. Interleukin-6 (IL-6) is a cytokine with a wide variety of biological functions. It is a potent inducer of fever and the acute phase response. The sequence of human IL-6 is known in the art and is described at UniProt Accession No. P05231. In one particular embodiment, the interleukin may be IL-6.

Alternatively, or additionally, the interleukin may be IL-12. Interleukin-12 (IL-12) is a T cell stimulating factor because it stimulates the growth and function of T cells. It is a heterodimeric cytokine comprised of IL-12A and IL-12B. The sequence of human IL-12A is known in the art and is described at UniProt Accession No. P29459 and the sequence of human IL-12B is also known and described at UniProt Accession No. P29460. In one particular embodiment, the interleukin may be IL-12.

In one embodiment, the panel comprises a cell free nucleosome or an epigenetic feature thereof and an interleukin. In another embodiment, the panel comprises an epigenetic feature of a cell free nucleosome and two interleukins. For example, the cell free nucleosome measurement can be combined with more than one interleukin measurement, such as IL-6 and IL-12. In a further embodiment, the epigenetic feature of a cell free nucleosome is selected from a histone isoform, such as H3.1, and a post translationally modified histone, such as H3cit. In a yet further embodiment, the panel of measurements is H3.1, H3cit, H4cit and IL-6.

In one embodiment, the panel comprises C-reactive protein (CRP). CRP is a pentameric protein found in plasma and levels of CRP (not adducted to nucleosomes) increase in plasma in response to inflammation, such as in bacterial, viral, fungal and microbial infections. CRP levels increase following IL-6 secretion by macrophages and T cells and its physiological role is to bind lysophosphatidylcholine expressed on the surface of dead or dying cells in order to activate the complement system via C1q. It also binds to phosphocholine on the surface of some bacteria and enhances phagocytosis. The measurement of CRP levels is useful for determining the progression of disease and the effectiveness of treatments and elevated CRP levels have been shown in patients with increased risk of diabetes, hypertension and cardiovascular disease. Increased CRP levels have also been found in patients with kidney failure and inflammatory bowel disease (IBD, including Crohn's disease and ulcerative colitis) and roughly correlate with coronary heart disease, although as elevated CRP is not directly related to heart disease it is not a specific prognostic marker. Since CRP is increased during inflammation, viral infections, such as SARS or coronavirus (e.g. COVID-19) may also lead to increased CRP levels in plasma.

In one embodiment, the panel comprises myeloperoxidase (MPO). MPO is expressed in neutrophil granulocytes and produces hypohalous acids to carry out their antimicrobial activity. It is stored in azurophilic granules and released into the extracellular space during degranulation. The levels of MPO (not measured adducted to nucleosomes) have been shown to be a useful predictor for myocardial infarction and have been combined with measurement of CRP (not measured adducted to nucleosomes) for increased accuracy in predicting myocardial infarction risk in patients.

It will be clear to those skilled in the art, that any combination of the biomarkers disclosed herein may be used in the monitoring method or device, such as the inline monitoring device, and that further markers may be added to a panel including these markers.

Apheresis Device

The invention provides a device configured to perform apheresis or ex vivo organ perfusion comprising one or more affinity matrices to bind and remove pathogenic substances. The term "affinity matrix" may refer to a solid support (e.g. a sepharose or polystyrene support) into which a ligand (e.g. a cfDNA-binding molecule) is immobilized or a solid support formed by the ligand itself (e.g. a water-insoluble DNA-binding polymer).

The affinity matrices may be placed into various affinity columns, or cartridges. For example, the apheresis ex vivo organ perfusion device can comprise a filtration cartridge and one or more affinity columns having an inlet and an outlet, in which the device is capable of capturing and removing target pathogenic substances from blood or plasma of a patient or from the liquid perfusate of the organ. The inlet and outlet can be positioned with respect to the affinity matrices such that blood/liquid perfusate entering the inlet must contact the affinity matrices before exiting through the outlet. Preferably, the geometry of the device is designed to maximize contact of blood (or plasma) or liquid perfusate with the affinity matrices during passage through the device. A variety of such designs are known in the art.

In some embodiments, the apheresis device comprises two or more affinity matrices. For example, a first affinity matrix may be capable of capturing a first pathogenic substance, such as nucleosome-bound cfDNA and/or exosome-bound cfDNA, and a second affinity matrix may be capable of capturing unbound cfDNA. The first and second affinity matrices are arranged within the device in any order.

Affinity matrices may include, for example, a DNA binding protein (e.g. a H1 histone), an anti-histone antibody (e.g. an anti-histone H2A antibody), an anti-nucleosome antibody (e.g. AN-1, AN-44), a DNA intercalating agent (e.g. a Hoechst dye), a DNA-binding polymer (e.g. a cationic/basic polymer, such as polyethylenimine, poly-L-lysine, poly-L-arginine, hexadimethrine bromide, amino terminated (—NH$_2$) polyamidoamine (PAMAM) dendrimer, polypropyleneimine (PPI) dendrimer; a non-ionic/neutral polymer, such as polyvinylpyrrolidone (PVP), polyvinylpolypyrrolidone (PVPP), poly (4-vinylpyridine-N-oxide); an anionic/acidic polymer; a linear polymer such as polyethylenimine, poly-L-lysine, poly-L-arginine; a branched polymer such as hyper-branched poly-L-lysine, hyper-branched polyethylenimine; or a dendrimeric polymer such as polyamidoamine (PAMAM) dendrimer, polypropyleneimine (PPI) dendrimer), an anti-DNA antibody (e.g. mouse monoclonal IgM Anti-ds+ss DNA antibody), a lectin (e.g. *Galanthus nivalis* Lectin (GNA), *Narcissus Pseudonarcissus* Lectin (NPA), Conconavalin A, phytohemagluttanin, or cyanovirin), and any combination thereof. An apheresis device, such as the device described in WO2019/053243, which is herein incorporated by reference, may be used in conjunction with the monitoring method or device, such as the inline monitoring device, of the invention.

Pathogenic Substances

The pathogenic substance to be removed from the blood of a subject during apheresis or from the liquid perfusate of the organ may be cell free DNA (cfDNA), such as nucleosome-bound cfDNA, exosome-bound cfDNA and/or unbound cfDNA.

As described herein, nucleosome-bound cfDNA might circulate in blood as mononucleosomes or higher order structures such as oligonucleosomes or chromatin fragments. Exosome-bound DNA refers to cfDNA present in exosomes which are small membrane vesicles (30-100 nm) of exocytotic origin secreted by most cell types. Exosomes might contain single-stranded DNA (ssDNA), mitochondrial DNA (mtDNA) and/or double-stranded (dsDNA) at the inner or outer space of the exosome. Unbound cfDNA refers to cfDNA not associated with another entity (i.e. particle-free circulating cfDNA) and may comprise dsDNA, ssDNA and oligonucleotides.

The pathogenic substance to be removed from the blood of a subject during apheresis or from the liquid perfusate may be neutrophil extracellular traps (NETs). NETs protect against infection by trapping invading pathogens, but, excessive or inappropriate NETosis is a major cause of pathology and is involved in a long and continually growing list of disease processes including, without limitation, all autoimmune conditions, all inflammatory conditions, Alzheimer's disease, atherosclerosis, bacterial infection, cystic fibrosis, pancreatitis, viral infection, diabetes, cancer, thrombosis, pneumonia, respiratory infections, gout and sepsis (for example, see Sollberger et al. (2018) Developmental Cell 44(5):542-553; Thalin et al. (2019) Arterioscler. Thromb. Vasc. Biol. 39:1724-1738; and Neubert et al. (2019) Frontiers in Immunology 10:12).

Inappropriate production of NETs is not only associated with these diseases but is a causative factor. The prolonged presence of NETs may cause tissue damage and development of an autoimmune reaction against NETs components leading to inflammatory, autoimmune, and vascular diseases. Cytotoxic proteases in NETs may cause endothelial damage in sepsis and small vessel vasculitis. In severe influenza the alveolar-capillary surfaces of the lungs may become embroiled with NETs and damaged by cytotoxic NETs-associated proteins including histones and MPO. NETs measurements in bronchoalveolar lavage fluid samples taken from patients with pneumonia and in serum samples taken from patients with COVID-19 infections have shown that NETs levels were higher in hospitalized patients receiving mechanical ventilation as compared with hospitalized patients breathing room air. NETs levels may therefore predict which patients are in need of high levels of respiratory support.

Most subjects infected with influenza or coronavirus experience mild illness. However, some population subgroups, including elderly persons aged over 60 years and persons with an underlying medical condition such as diabetes, chronic lung conditions and particularly chronic cardiac conditions, are at risk of severe effects including ARS, SARS, pneumonia and death. The exact mechanism by which influenza or coronavirus infection leads to complications including pneumonia is not clear, but it is thought to be caused by a hyperimmune reaction to the viral infection in which excessive NETs contribute to acute injury of the lung leading to pneumonia and, in the worst cases, death.

In cancer, NETs are implicated as a cause of cancer related thrombosis and as a facilitator of metastatic stage IV cancer disease progression by a variety of mechanisms including through the entrapment of tumour cells in NETs, facilitating the spread of NET-bound tumour cells around the body and by assisting in the establishment of metastatic cell growth at new locations. Therefore, it is clear that NETs are associated with, and/or a causative factor in a wide variety of disease processes.

In one embodiment, the subject has a disease characterized by an elevated level of NETs and/or cfDNA in the blood. Increased levels of circulating cfDNA is a recognised marker for a number of diseases and pathological conditions including but not limited to sepsis, cancer (including metastatic cancer), acute organ failure, organ infarct (including myocardial infarction and ischemic stroke), hemorrhagic stroke, autoimmune disorders, graft-versus-host-disease (GVHD), graft rejection, systemic inflammatory response syndrome (SIRS), multiple organ dysfunction syndrome (MODS), traumatic injury, proinflammatory status in aged individuals, diabetes, atherosclerosis, neurodegenerative disease, eclampsia, infertility, coagulation disorder, pregnancy-associated complications and infection. Therefore, apheresis devices, such as those described in WO2019/ 053243, U.S. Pat. No. 9,364,601, US2007/0092509 or Kusaoi et al. Ther. Apher. Dial. (2016) 20: 348-353, which are herein incorporated by reference, may be used to remove cfDNA from a subject suffering with one of these diseases.

In one embodiment, the subject is suffering from an infection. In a further embodiment, the subject is suffering from sepsis or septic shock.

The infection may be, for example, a respiratory tract infection. In one embodiment, the respiratory tract infection is selected from: influenza, pneumonia and severe acute respiratory syndrome (SARS). SARS is a respiratory infection caused by the SARS coronavirus (SARS-CoV) and other, related coronaviruses are known (e.g. COVID-19 (also known as SARS-CoV-2 and previously as 2019-nCoV)). It is known to cause fever flu-like symptoms, cough and lethargy and can lead to pneumonia (e.g. direct viral pneumonia or secondary bacterial pneumonia).

Monitoring Methods

According to a further aspect, there is provided a method of monitoring a subject during an extracorporeal procedure comprising: passing the blood of the subject through the extracorporeal device described herein; and monitoring the level of cell free nucleosomes in the blood of the subject using the monitoring method or device of the extracorporeal device. In one embodiment, the extracorporeal procedure is an apheresis procedure and the extracorporeal device is an apheresis device. In a further embodiment, the level of cell free nucleosomes in the blood of the subject is monitored using the inline monitoring device of the apheresis device.

In one embodiment, the duration, such as the length, of the apheresis procedure is determined based upon the level of cell free nucleosomes in the blood of the subject measured using the monitoring method or device, such as the inline monitoring device. The monitoring device finds particular use in monitoring when the apheresis procedure should be finished, e.g. because the level of cell free nucleosomes has reached an acceptable level. This makes treatment more efficient and effective because the subject is only attached to the apheresis device for as long as necessary.

In one embodiment, more than one measurement, such as two inline measurements, are made in the blood, plasma or liquid perfusate before and after the point where blood, plasma or liquid perfusate contacts the solid phase binder for nucleosomes (e.g. at positions 1 and 2 in FIG. 1) to monitor both the level of nucleosomes in the blood of the subject or in the liquid perfusate of the organ and also to monitor the efficacy of the nucleosome depletion of the solid phase binder.

Detecting and/or quantifying the level of cell free nucleosomes present may include determining the concentration of the cell free nucleosomes.

In one embodiment, the method of detection or measurement comprises: (i) contacting the sample with a first binding agent which binds to a cell free nucleosome or component thereof; and (ii) detecting or quantifying the binding of the second binding agent in the sample. In one embodiment, the monitoring method or device, such as the inline monitoring device, is configured to measure the level of cell free nucleosomes by an immunochemical or biosensor method.

The detection or measurement may comprise an immunoassay, immunochemical, mass spectroscopy, chromatographic, chromatin immunoprecipition or biosensor method. In particular, detection and/or measurement may comprise a 2-site immunoassay method for nucleosome moieties. Such a method is preferred for the measurement of nucleosomes or nucleosome incorporated epigenetic features in situ employing two anti-nucleosome binding agents or an anti-nucleosome binding agent in combination with an anti-histone modification or anti-histone variant or anti-DNA modification or anti-adducted protein detection binding agent. Also, detection and/or measurement may comprise a 2-site immunoassay, for example employing combinations of a labelled or immobilized: anti-nucleosome, anti-histone modification, anti-histone variant/isoform, anti-DNA modification or anti-adducted protein binding agent.

Detecting or measuring the level of the biomarker(s) may be performed using one or more reagents, such as a suitable binding agent. For example, the one or more binding agents may comprise a ligand or binder specific for the desired biomarker, e.g. nucleosomes or component part thereof, an epigenetic feature of a nucleosome, a structural/shape mimic of the nucleosome or component part thereof, optionally in combination with one or more interleukins.

It will be clear to those skilled in the art that the terms "antibody", "binder" or "ligand" as used herein are not limiting but are intended to include any binder capable of binding to particular molecules or entities and that any suitable binder can be used in the method of the invention. It will also be clear that the term "nucleosomes" is intended to include mononucleosomes, oligonucleosomes, NETs and any protein-DNA chromatin fragments that can be analysed in fluid media.

Methods of detecting biomarkers are known in the art. The reagents may comprise one or more ligands or binders, for example, naturally occurring or chemically synthesised compounds, capable of specific binding to the desired target. A ligand or binder may comprise a peptide, an antibody or a fragment thereof, or a synthetic ligand such as a plastic antibody, or an aptamer or oligonucleotide, capable of specific binding to the desired target. The antibody can be a monoclonal antibody or a fragment thereof. It will be understood that if an antibody fragment is used then it retains the ability to bind the biomarker so that the biomarker may be detected (in accordance with the present invention). A ligand/binder may be labelled with a detectable marker, such as a luminescent, fluorescent, enzyme or radioactive marker; alternatively or additionally a ligand according to the invention may be labelled with an affinity tag, e.g. a biotin, avidin, streptavidin or His (e.g. hexa-His) tag. Alternatively, ligand binding may be determined using a label-free technology for example that of ForteBio Inc.

Methods of the invention may involve normalisation of marker levels. For example, the level of cell free nucleosomes containing a particular epigenetic feature may be normalised against the level of nucleosomes per se (or some other type of nucleosomes or parameter) to express the level as a proportion of nucleosomes containing the feature. For example, to express the level of citrullinated nucleosomes as the proportion of nucleosomes that are citrullinated.

As used herein, the term "biosensor" means anything capable of detecting the presence of the biomarker. Examples of biosensors are described herein. Biosensors may comprise a ligand binder or ligands, as described herein, capable of specific binding to the biomarker. Such biosensors are useful in detecting and/or quantifying a biomarker of the invention.

Suitably, biosensors for detection of one or more bio-markers combine biomolecular recognition with appropriate means to convert detection of the presence, or quantitation, of the biomarker in the sample into a signal. Biosensors can be adapted for "alternate site" diagnostic testing, e.g. in the ward, outsubjects' department, surgery, home, field and workplace. Biosensors to detect one or more biomarkers of the invention include acoustic, plasmon resonance, holographic, Bio-Layer Interferometry (BLI) and microengineered sensors. Imprinted recognition elements, thin film transistor technology, magnetic acoustic resonator devices and other novel acousto-electrical systems may be employed in biosensors for detection of the one or more biomarkers.

The immunoassays described herein include any method employing one or more antibodies or other specific binders directed to bind to the biomarkers defined herein. Immunoassays include 2-site immunoassays or immunometric assays employing enzyme detection methods (for example ELISA), fluorescence labelled immunometric assays, time-resolved fluorescence labelled immunometric assays, chemiluminescent immunometric assays, immunoturbidimetric assays, particulate labelled immunometric assays and immunoradiometric assays as well as single-site immunoassays, reagent limited immunoassays, competitive immunoassay methods including labelled antigen and labelled antibody single antibody immunoassay methods with a variety of label types including radioactive, enzyme, fluorescent, time-resolved fluorescent and particulate labels. All of said immunoassay methods are well known in the art, see for example Salgame et al. (1997) and van Nieuwenhuijze et al. (2003).

Identifying, detecting and/or quantifying can be performed by any method suitable to identify the presence and/or amount of a specific protein in a biological sample from a subject or a purification or extract of a biological sample or a dilution thereof. In particular, quantifying may be performed by measuring the concentration of the target in the sample or samples. Biological samples that may be tested in a method of the invention include those as defined hereinbefore. The samples can be prepared, for example where appropriate diluted or concentrated, and stored in the usual manner. The present invention finds particular use in plasma samples which may be obtained from the subject.

Identification, detection and/or quantification of biomarkers may be performed by detection of the biomarker or of a fragment thereof, e.g. a fragment with C-terminal truncation, or with N-terminal truncation. Fragments are suitably greater than 4 amino acids in length, for example 5, 6, 7, 8, 9, 10, 11, 12, 13, 14, 15, 16, 17, 18, 19, or 20 amino acids in length. It is noted in particular that peptides of the same or related sequence to that of histone tails are particularly useful fragments of histone proteins.

Methods involving detection and/or quantification of one or more biomarkers of the invention can be performed on bench-top instruments, or can be incorporated onto disposable, diagnostic or monitoring platforms that can be used in a non-laboratory environment, e.g. in the physician's office or at the subject's bedside. Suitable biosensors for performing methods of the invention include "credit" cards with optical or acoustic readers. Biosensors can be configured to allow the data collected to be electronically transmitted to the physician for interpretation and thus can form the basis for e-medicine.

Detecting and/or quantifying may be compared to a cut-off level. Cut-off values can be predetermined by analysing results from multiple patients and controls, and determining a suitable value for classifying a subject as with or without the disease. For example, for diseases where the level of biomarker is higher in patients suffering from the disease, then if the level detected is higher than the cut-off, the patient is indicated to suffer from the disease. Alternatively, for diseases where the level of biomarker is lower in patients suffering from the disease, then if the level detected is lower than the cut-off, the patient is indicated to suffer from the disease. The advantages of using simple cut-off values include the ease with which clinicians are able to understand the test and the elimination of any need for software or other aids in the interpretation of the test results. Cut-off levels can be determined using methods in the art.

Detecting and/or quantifying may also be compared to a control. It will be clear to those skilled in the art that the control subjects may be selected on a variety of basis which may include, for example, subjects known to be free of the disease or may be subjects with a different disease (for example, for the investigation of differential diagnosis). The "control" may comprise a healthy subject, a non-diseased subject and/or a subject without an infection.

Therefore, in one embodiment, the method additionally comprises comparing the level of cell free nucleosomes or component thereof with one or more controls. For example, the method may comprise comparing the level of cell free nucleosomes obtained from the subject with the level of cell free nucleosomes obtained from a normal subject. The control may be a healthy subject.

It will be understood that it is not necessary to measure controls levels for comparative purposes on every occasion. For example, for healthy/non-diseased controls, once the 'normal range' is established it can be used as a benchmark for all subsequent tests. A normal range can be established by obtaining samples from multiple control subjects without an infection and testing for the level of biomarker. Results (i.e. biomarker levels) for subjects suspected to have an infection can then be examined to see if they fall within, or outside of, the respective normal range. Use of a 'normal range' is standard practice for the detection of disease.

In one embodiment, the method additionally comprises determining at least one clinical parameter for the patient. This parameter can be used in the interpretation of results. Clinical parameters may include any relevant clinical information for example, without limitation, body temperature, gender, weight, Body Mass Index (BMI), smoking status and dietary habits. Therefore, in one embodiment, the clinical parameter is selected from the group consisting of: body temperature, age, sex and body mass index (BMI).

Methods of Treatment

According to a further aspect, there is provided a method of treating a disease in a subject in need thereof comprising: passing the blood of the subject through the extracorporeal device described herein; and monitoring the level of cell free nucleosomes in the blood of the subject using the monitoring method or device of the extracorporeal device. In one embodiment, the extracorporeal device is an apheresis device and passing the blood of the subject through the apheresis device removes one or more pathogenic substances from the blood of the subject. In a further embodiment, the level of cell free nucleosomes in the blood of the subject is monitored using the inline monitoring device of the apheresis device.

The apheresis procedure is performed by passing the blood of the subject through the apheresis device to remove one or more pathogenic substances from the blood of the subject. Therefore, in one embodiment, the apheresis procedure is terminated (i.e. finished) when the level of cell free nucleosomes in the blood of the subject is determined to be an acceptable level.

As described herein, the subject may have a disease characterized by an elevated level of neutrophil extracellular traps and/or cfDNA in the blood. The method of treatment therefore involves removing these substances from the blood in order to treat the disease. Therefore, in another aspect there is provided a method of reducing the level of cfDNA in the blood of a patient comprising (a) performing an apheresis procedure comprising diverting blood or plasma from the patient into an apheresis device as described herein to produce purified blood or plasma with reduced levels of cfDNA; (b) returning the purified blood or plasma to the patient and (c) monitoring the level of cell free nucleosomes in the blood of the subject using the monitoring method or device, such as the inline monitoring device, of the apheresis device to determine when the level of cfDNA in the blood of the patient has been sufficiently reduced. The apheresis procedure may reduce the level of substantially all types of cfDNA in the patient's blood, including nucleosome-bound cfDNA, exosome-bound cfDNA and unbound cfDNA (including dsDNA, ssDNA and oligonucleotides).

The duration (i.e. length) of the apheresis procedure may be determined based upon the level of cell free nucleosomes in the blood of the subject measured using the monitoring method or device, such as using the inline monitoring device. Furthermore, it will be understood that the method may comprise repeating the apheresis procedure on one or more occasions.

Diseases which may treated by apheresis include neurological disorders (including Acute inflammatory demyelinating polyneuropathy or Guillain-Barré syndrome, Chronic inflammatory demyelinating polyradiculoneuropathy, Paraproteinemic demyelinating polyneuropathies PANDAS, sydenham's chorea, Chronic focal encephalitis, Lambert-Eaton myasthenic syndrome, Multiple Sclerosis or MS and Neuromyelitis optica), Renal disorders (including Antineutrophil cytoplasmic antibody (ANCA)-associated rapidly progressive glomerulonephritis or Wegener's Granulomatosis, anti-glomerular basement membrane antibodies or Goodpasture's syndrome, Antibody-mediated renal transplant rejection, and Recurrent focal segmental glomerular sclerosis), Haematological disorders (including Atypical haemolytic uraemic syndrome or aHUS, autoantibody to factor H, Hyperviscosity in monoclonal gammapathies or paraproteinaemias, Severe/symptomatic cryoglobulinaemia, Thrombotic thrombocytopenic purpura, ABO-incompatible haemopoietic stem cell transplantation, Myeloma with cast nephropathy and Red cell alloimmunisation in pregnancy), immunological disorders (including Catastrophic antiphospholipid syndrome and Cerebral systemic lupus erythematosus or SLE) and metabolic disorders (including Familial hypercholesterolaemia and Wilson's disease) (de Back et al. (2019) Transfusion and Apheresis Science 58: 254-257).

In some embodiments, the method is effective to treat a disorder in a patient, wherein the disorder is selected from sepsis, cancer (including metastatic cancer), acute organ failure, organ infarct (including myocardial infarction, ischemic stroke, hemorrhagic stroke) graft rejection, systemic inflammatory response syndrome (SIRS); multiple organ dysfunction syndrome (MODS); graft-versus-host-disease (GVHD), traumatic injury, proinflammatory status in aged individuals, diabetes, atherosclerosis, neurodegenerative disease, autoimmune disease, eclampsia, infertility, coagulation disorder, pregnancy-associated complications and infection. In a further embodiment, the disorder is selected from sepsis, cancer or acute organ failure. In a yet further embodiment, the disorder is sepsis. In an alternative embodiment, the disorder is cancer.

In a further aspect of the invention, there is provided an ex vivo organ perfusion method or device that incorporates the measurement of NETs, nucleosomes or cfDNA. Organs obtained from an organ donor for transplantation into a recipient subject may deteriorate during storage or transport. Mild deterioration may lead to a poorer outcome for the recipient patient. Severely deteriorated organs cannot be used for transplantation and must be discarded. In the USA in 2018, 13.2% of organs recovered for transplantation were discarded including 3755 kidneys, 278 pancreata, 707 livers, 3 intestines, 23 hearts, and 317 lungs (Israni et al; *Am J Transplant* 2019; 20 (Suppl 1): 509-541. doi: 10.1111/ajt.15678). This organ deterioration is related to an inflammatory response in the donor organ and the formation of NETs is a major contributor to donor organ damage (Caldarone et al, Eur Respir J 2019; 53: 1801736 [https://doi.org/10.1183/13993003.01736-2018]). To help maintain donor organ viability, organs may be perfused ex vivo with plasma and further protection may be afforded to the donor organ by monitoring and removal of NETs in the device and the organ. In this aspect of the invention, the health and viability for transplant of a donor organ perfused in an ex vivo perfusion device can be monitored by the measurement of NETs or nucleosomes or cfDNA. This monitoring also provides an early warning of the risk of deterioration of the donor organ and an indicator of the need for treatment of the organ (for example by the removal of NETs).

It will be understood that the embodiments described herein may be applied to all aspects of the invention, i.e. the embodiment described for the uses may equally apply to the claimed methods and so forth.

The invention will now be illustrated with reference to the following non-limiting examples.

Example 1

FIG. 1 shows an example inline nucleosome measurement in plasma prior to adsorption of nucleosomes and NETs by the matrix in the NETs absorber (for example containing immobilised histone H1) at position 1. Measurements may be taken at other points (for example without limitation positions 2-5 as shown in FIG. 1). Measurements may also be taken at multiple points. The measurements are made in whole blood or plasma before and after the NETs adsorber to provide real time information on the both the current circulating nucleosome levels in the subject as well on the effectiveness of nucleosome/NETs depletion of the NETs adsorber.

Example 2

Figure 2:
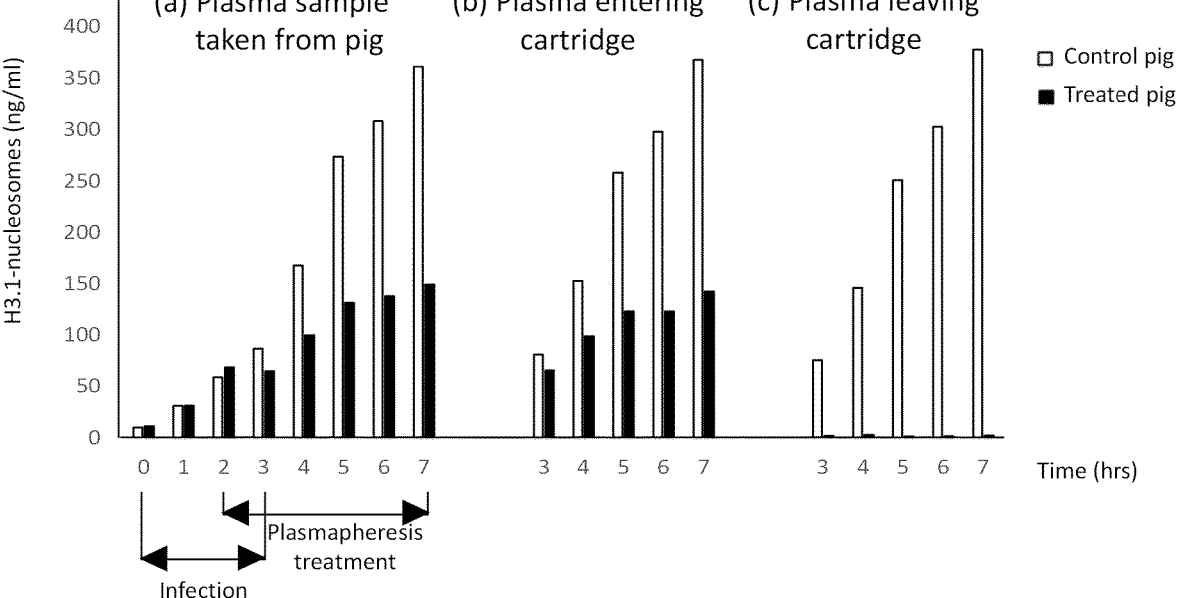
FIG. 2. Results from the experiment described in Example 2 showing the mean levels of nucleosomes containing histone isoform H3.1 measured in 16 pigs induced with sepsis placed on plasmapheresis. In 9 pigs, plasma was passed through a cartridge containing NET binders (treated, closed bars) and in 7 pigs, plasma was passed through a control cartridge which did not contain a NETs binder (control, open bars).
Figure 3:
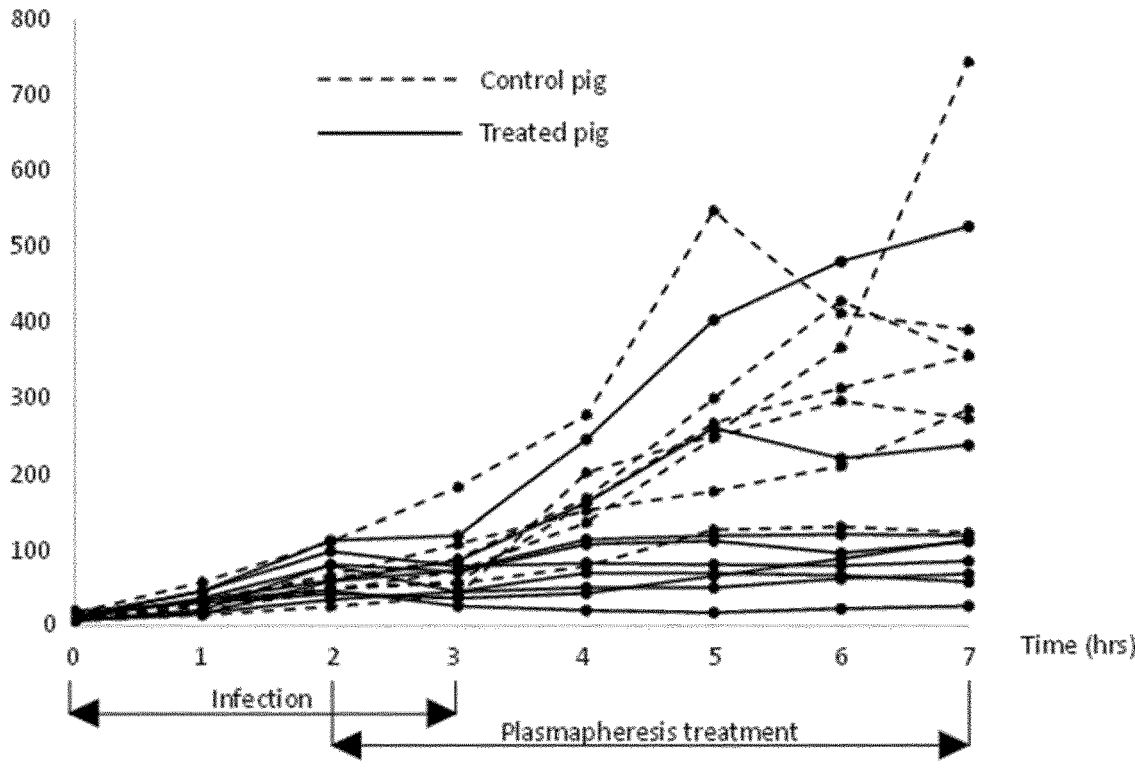
FIG. 3. Results from the experiment described in Example 2 and shown in FIG. 2, but for levels in individual test subjects.
Figure 3:
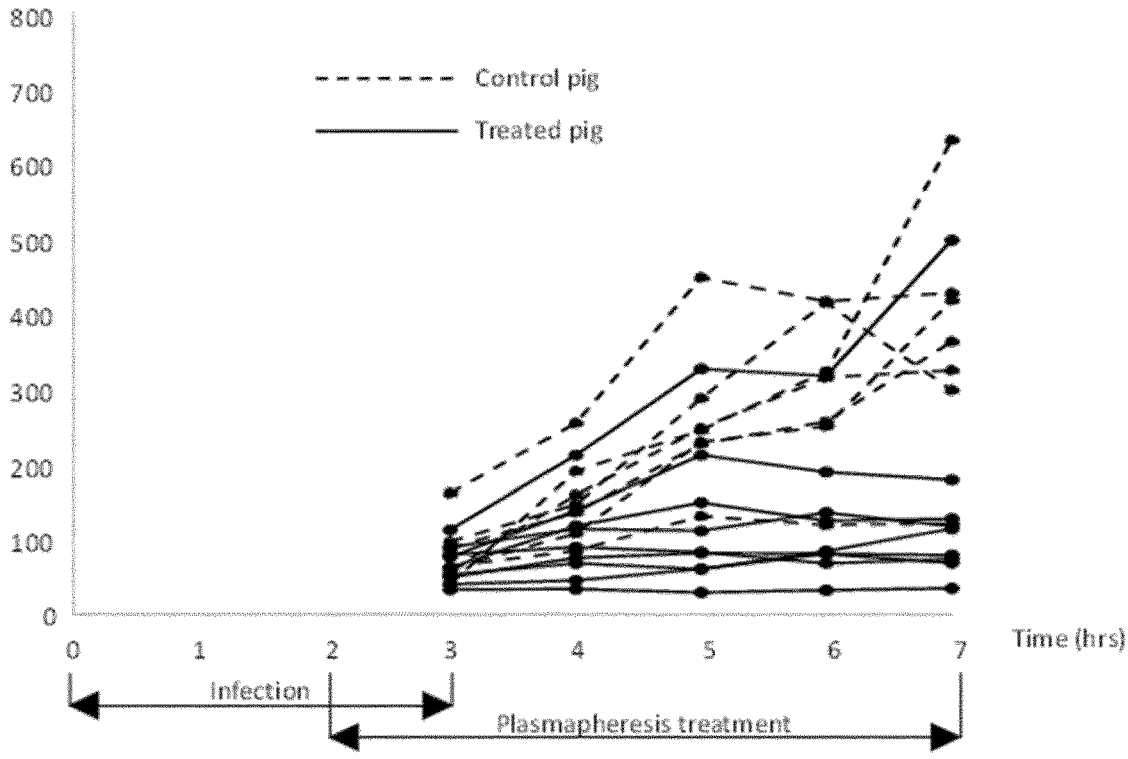

Sepsis was induced in 16 pigs by infection by infusion of high doses of *Escherichia coli* (*E. coli*) bacteria administered intravenously over 3 hours (0-3 hours in FIGS. 2 and 3). The septic pigs were treated by a plasmapheresis method to remove NETs from the blood stream as described in WO2019053243. Briefly, whole blood was removed from the body of the pig through a tube into a plasmapheresis device, the whole blood was separated into a cell fraction and a plasma fraction, the plasma was passed through a plasmapheresis cartridge containing a binder of NETs to remove NETs from the plasma, the plasma was then rejoined with the blood cells and returned to the body of the pig. The plasmapheresis treatment was performed over 5 hours (2-7 hours in FIGS. 2 and 3). The plasmapheresis cartridges used for 9 of the pigs contained the NETs binder (treated pigs) and the cartridges used for the other 7 pigs contained no binder (control pigs).

Eight plasma samples were collected hourly, at time points 0-7 hours post commencement of infection, from each pig for measurements of circulating nucleosomes to ascertain whether the method of the invention was (i) effective as a monitor for the course of the infection and (ii) effective as a monitor for efficacy of the treatment.

In addition, plasma samples were collected from the plasmapheresis device, both upstream of the cartridge (to sample the plasma entering the NETs binder cartridge) and downstream of the cartridge (to sample the plasma leaving the NETs binder cartridge) to ascertain whether the extent of the depletion of the plasma by the NETs binder in the cartridge could be monitored by methods of the invention. Five upstream and five downstream samples were taken hourly at time points 3-7 hours post commencement of infection (3-7 hours in FIGS. 2 and 3).

The plasma samples were assayed for nucleosomes containing histone isoform H3.1 (H3.1-nucleosome) levels. Assay measurements for were performed by immunoassay using an automated immunoassay instrument. Briefly, calibrant or sample (50 µl) was incubated with an acridinium ester labelled anti-nucleosome antibody (50 µl) and assay buffer (100 µl) for 1800 seconds at 37° C. Magnetic beads coated with an anti-histone H3.1 antibody (20 µl) were added and the mixture was incubated a further 900 seconds. The magnetic beads were then isolated, washed 3 times and magnetic bound acridinium ester was determined by luminescence output over 7000 milliseconds.

Mean results for circulating H3.1-nucleosome levels in the control pigs and treated pigs are shown in FIG. 2a. The control pigs (infected to induce sepsis but not treated) developed sepsis over the following hours and this was reflected in an observed rise in circulating H3.1-nucleosome levels. The rise in mean H3.1-nucleosome levels was clear at 1 hour (post commencement of infection) and accelerated after 3 hours which is consistent with the time course of the NETosis process. The H3.1-nucleosome levels continued to rise and reached 361 ng/ml at 7 hours. A similar initial rise in mean circulating H3.1-nucleosome levels was observed in the treated pigs from 0-2 hours. Initiation of plasmapheresis treatment at 2 hours resulted in a slowing of the increase in nucleosome levels and the mean level observed at 7 hours was 150 ng/ml. This is considerably lower than the mean level observed in the control pigs which demonstrates the effectiveness of the plasmapheresis method and shows that the level of H3.1 nucleosomes is an effective monitor and treatment guide for the course and extent of the sepsis disease and an effective monitor for the NETosis process in vivo.

Mean results for plasma H3.1-nucleosome levels measured in samples taken from within the plasmapheresis device upstream from the cartridge during operation are shown in FIG. 2b. These results are similar to those observed for the mean circulating H3.1-nucleosome levels measured shown in FIG. 2a.

Mean results for plasma H3.1-nucleosome levels measured in samples taken from within the plasmapheresis device downstream from the cartridge during operation are shown in FIG. 2c. For the control pigs, the results of FIG. 2c are similar to those in FIGS. 2b (and 2a) showing that passing plasma through a cartridge containing no binder of NETs did not significantly affect the observed H3.1-nucleosome level. This is consistent with the expected outcome that the level of NETs in plasma was not significantly affected by passage through a cartridge containing no binder of NETs. For the treated pigs, the results of FIG. 2c are all low. This is consistent with the expected outcome that passing plasma through a cartridge containing a binder of NETs resulted in the removal of most or all NETs from the plasma. Moreover, the results show that NETs binder within the cartridge was not saturated with NETs at 7 hours and continued to bind all or most of the NETs present in plasma entering the device. Measurements of the level of H3.1-nucleosomes are therefore useful to determine when the binding material within a cartridge has become saturated and is hence no longer useful as a tool for the removal of NETs and should be exchanged for a fresh cartridge.

The combined results of FIGS. 2b and 2c therefore show that measurements of the level of H3.1-nucleosomes are useful as a monitor and a guide for treatments for NETosis and sepsis.

The results for circulating H3.1-nucleosome levels measured in samples taken from all 16 pigs are shown individually in FIG. 3a. The mean H3.1-nucleosome level observed in control pigs at 7 hours was 361 ng/ml and the level was above 120 ng/ml in all control pigs (range 123-743 ng/ml). In contrast, the mean H3.1-nucleosome level observed in treated pigs at 7 hours was 150 ng/ml and the level was below 120 ng/ml in most (7 of 9) treated pigs (range 27-526 ng/ml). The results demonstrate the effectiveness of the plasmapheresis treatment method. The results also show that the level of H3.1 nucleosomes is an effective monitor and treatment guide for the course and extent of sepsis disease and an effective monitor and treatment guide for excessive NETosis in vivo. Moreover, the results in FIG. 3a show that measurements of circulating H3.1-nucleosome levels can be used to identify individuals with elevated levels of NETs as suitable candidates for treatments to reduce levels of NETs or NETosis.

Results for plasma H3.1-nucleosome levels measured in samples taken from within the plasmapheresis device upstream from the cartridge during operation are shown individually for all 16 pigs in FIG. 3b. As described above for FIG. 2, the results shown in FIG. 3b are similar to those in FIG. 3a. The mean H3.1-nucleosome level observed in control pigs at 7 hours was 368 ng/ml (range 121-629 ng/ml). In contrast, the H3.1-nucleosome level observed in treated pigs at 7 hours was lower with a mean result of 143 ng/ml (range 34-497 ng/ml).

Results for plasma H3.1-nucleosome levels measured in samples taken from within the plasmapheresis device downstream from the cartridge during operation are shown individually for all 16 pigs in FIG. 3c. The mean level of H3.1-nucleosomes measured for control pigs at 7 hours was 378 ng/ml (range 147-617 ng/ml). In contrast, the mean level of H3.1-nucleosomes observed in plasma downstream of the cartridge at 7 hours for treated pigs was 2.4 ng/ml (range 0.7-6.5 ng/ml) and was below 7 ng/ml at all time points for all 9 treated pigs.

The combined results of FIGS. 3b and 3c show that measurements of the level of H3.1-nucleosomes are useful as a monitor and a guide for treatments for NETosis and sepsis.

Example 3

Figure 4:
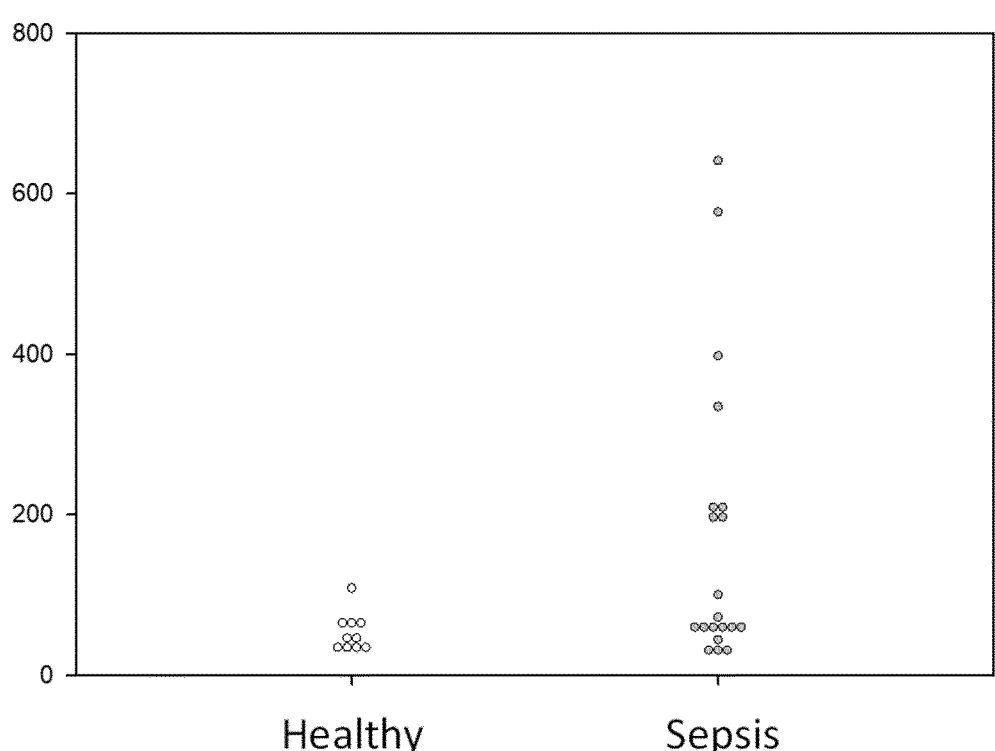
FIG. 4. H3.1-nucleosome levels measured in human subjects diagnosed with sepsis and healthy human subjects.

Plasma samples were obtained from 20 human subjects diagnosed with sepsis and 10 healthy human subjects. The plasma samples were assayed for nucleosomes containing histone isoform H3.1 (H3.1-nucleosome) levels using an automated immunoassay instrument as described in EXAMPLE 2. Elevated levels were observed in sepsis samples compared to healthy subjects, which is likely due to the effect of NETosis in various stages of this disease (FIG. 4).

Example 4

Plasma samples were obtained from 52 patients admitted to the German Heart Center, Clinic at the Technical University Munich. Fourteen of the patients were tested as positive for COVID-19 by qRTPCR, including 5 non-hospitalized patients with mild disease attending outpatient clinics or attending the Emergency Room (ER), 3 patients with more serious disease (but not requiring intensive care) hospitalized in standard normal dependency wards and 6 patients with severe disease hospitalized and admitted to intensive care. Four of the 6 patients requiring intensive care did not survive.

Plasma samples were also obtained from 38 patients tested as negative for COVID-19 by qRTPCR, including 11 recruited at outpatient clinics or ER, 22 on standard wards and 5 admitted to intensive care.

The plasma samples were assayed for H3.1-nucleosome levels using a different format of the immunoassay described in EXAMPLE 2 employing the same antibodies. The level of H3.1-nucleosomes was low in the COVID negative patients and higher in the COVID positive patients. The H3.1-nucleosome levels measured in the COVID positive patients with more serious disease (in standard hospital wards) were higher than those measured in non-hospitalized patients with mild disease. The H3.1-nucleosome levels measured in the COVID positive patients with severe disease (in intensive care) were higher than those measured in patients admitted to standard hospital wards. Moreover, the 4 patients who did not survive had the 4 highest levels detected among any subjects. The data show that H3.1-nucleosome levels (and H3R8Cit-nucleosome levels) track the trajectory of the disease in human subjects and can be used to monitor nucleosome and NETs levels in response to treatment. The data in this EXAMPLE 4 is published in Cavalier et al. (2021) Front. Mol. Biosci. 8:600881. doi: 10.3389/fmolb.2021.600881.

Example 5

Plasma samples were obtained from 20 patients on admission to hospital with severe COVID-19 requiring organ support in an intensive care unit (ITU) and from 28 patients with non-severe COVID-19 requiring hospitalization but not requiring organ support.

The plasma samples were assayed for H3.1-nucleosome levels using a different format of the immunoassay described in EXAMPLE 2 employing the same antibodies. The H3.1-nucleosome levels measured in the non-severe COVID-19 patients were highly elevated. However, the levels measured in the severe COVID-19 patients were extremely elevated and higher than the levels in the non-severe COVID-19 patients. The data show that H3.1-nucleosome levels track the trajectory of the disease in human subjects and can be used to monitor nucleosome and NETs levels in response to treatment. The data in this EXAMPLE 5 is published in Rea et al. (2021) ISTH Academy. Rea C. Jul. 17, 2021; 326469; PB0268.

Example 6

Serial plasma samples were obtained from 20 patients with severe COVID-19 requiring organ support on admission to hospital and on day 3, 7 10. Six of the patients died within 28 days.

The plasma samples were assayed for H3.1-nucleosome levels using a different format of the immunoassay described in EXAMPLE 2 employing the same antibodies. The H3.1-nucleosome levels measured on admission in the severe COVID-19 patients were extremely elevated. Moreover, the highest levels were observed in the patients who subsequently died and this differential was maintained during day 1-7 of admission to ITU. The data show that H3.1-nucleosome levels track the trajectory of the disease in human subjects and can be used to monitor nucleosome and NETs levels in response to treatment and for assessment of prognosis. The data in this EXAMPLE 6 is published in Rea et al. (2021) ISTH Academy. Rea C. Jul. 17, 2021; 326469; PB0268.

Example 7

Serial plasma samples were obtained from 3 patients with COVID-19 on admission to hospital and daily until day 10 and weekly thereafter until discharge from hospital. One of the patients was admitted directly to ITU. The second patient was admitted to a normal medical ward and remained there for the duration of their stay in hospital. The third patient was admitted to a normal medical ward but was transferred to ITU on day 5 of their stay in hospital.

The plasma samples were assayed for H3.1-nucleosome levels using a different format of the immunoassay described in EXAMPLE 2 employing the same antibodies.

The H3.1-nucleosome levels measured in the patient admitted directly to ITU were high on admission (around 1000 ng/ml) and remained high for 10-12 days. Treatment was successful and the level fell dramatically thereafter (to around 500 ng/ml) and remained at this level. The patient was discharged from ITU at approximately 3 weeks.

The H3.1-nucleosome levels measured in the second patient who was admitted to a normal medical ward and remained there for the duration of their stay in hospital, was around 500 ng/ml on admission and remained at approximately this level for a week. Treatment was successful and the level fell thereafter to around 300 ng/ml until discharge on day 10.

The H3.1-nucleosome levels measured in the third patient was around 1200 ng/ml on admission to a normal medical ward. However, treatment in the medical ward was not successful and the patient was transferred to ITU on day 5. Concomitantly, the H3.1-nucleosome levels rose to reach a peak of around 1400 ng/ml on day 5 reflecting the worsening condition of the patient. The subsequent treatment in ITU was successful and the measured H3.1-nucleosome level fell to around 800 ng/ml by day 8 and to around 300 ng/ml by day 24.

The lower levels were maintained and the patient was discharged from ITU on around day 33 day.

The data show that H3.1-nucleosome levels track the trajectory of the disease, both in amelioration and deterioration of disease, in individual human subjects and can be used to monitor nucleosome and NETs levels in response to treatment and for assessment of prognosis. The data in this EXAMPLE 7 is published in Stanford et al. (2021) ISTH Academy. Rea C. Jul. 17, 2021; 326469; PB0268.

CLAUSES

1. An apheresis device comprising one or more affinity matrices for removing one or more pathogenic substances from the blood of a subject and an inline monitoring device for measuring the level of cell free nucleosomes present in the blood of the subject.

2. The apheresis device of clause 1, wherein the inline monitoring device measures the level of cell free nucleosomes present in the blood of the subject in real-time.

3. The apheresis device of clause 1 or clause 2, wherein the inline monitoring device comprises a solid phase with immobilized binding agents for binding cell free nucleosomes.

4. The apheresis device of clause 3, wherein the binding agent binds to a feature of a core nucleosome that is common to all or most nucleosomes.

5. The apheresis device of clause 3, wherein the binding agent binds to an epigenetic feature of cell free nucleosomes.

6. The apheresis device of clause 5, wherein the epigenetic feature is a histone isoform (such as a histone isoform of a core nucleosome, in particular a histone H3 isoform) or a histone post translational modification (such as a histone PTM of a core nucleosome, in particular a histone H3 or H4 PTM), a particular nucleotide associated with a cell free nucleosome and a protein adduct associated with a cell free nucleosome.

7. The apheresis device of clause 5 or clause 6, wherein the epigenetic feature is a histone post translation modification selected from citrullination.

8. The apheresis device of any one of clauses 1 to 7, wherein the inline monitoring device is configured to measure the level of cell free nucleosomes by an immunochemical or biosensor method.

9. The apheresis device of any one of clauses 1 to 8, wherein the inline monitoring device comprises a panel of markers to be measured in the blood of the subject.

10. The apheresis device of any one of clauses 1 to 9, wherein the inline monitoring device additionally comprises binding agents to detect one or more interleukins present in the blood of the subject, such as IL-6 and/or IL-12.

11. The apheresis device of any one of clauses 1 to 10, wherein the inline monitoring device additionally comprises binding agents to detect one or more protein markers, such as C reactive protein (CRP), myeloperoxidase (MPO), D-Dimer and/or factor VII-activating protease (FSAP).

12. The apheresis device of any one of clauses 1 to 11, wherein the pathogenic substance is cell free DNA (cfDNA), such as nucleosome-bound cfDNA, exosome-bound cfDNA and/or unbound cfDNA.

13. The apheresis device of any one of clauses 1 to 12, wherein the one or more affinity matrices are arranged in one or more affinity columns.

14. The apheresis device of any one of clauses 1 to 13, wherein the subject is a human or an animal subject.

15. A method of monitoring a subject during an apheresis procedure comprising: passing the blood of the subject through the apheresis device of any one of clauses 1 to 14; and monitoring the level of cell free nucleosomes in the blood of the subject using the inline monitoring device of the apheresis device.

16. The method of clause 15, wherein the length of the apheresis procedure is determined based upon the level of cell free nucleosomes in the blood of the subject measured using the inline monitoring device.

17. A method of treating a disease in a subject in need thereof comprising: passing the blood of the subject through the apheresis device of any one of clauses 1 to 14 to remove one or more pathogenic substances from the blood of the subject; and monitoring the level of cell free nucleosomes in the blood of the subject using the inline monitoring device of the apheresis device.

18. The method of clause 17, wherein the apheresis procedure is finished when the level of cell free nucleosomes in the blood of the subject is determined to be an acceptable level.

19. The method of clause 17 or clause 18, wherein the subject has a disease characterized by an elevated level of neutrophil extracellular traps and/or cfDNA in the blood.

20. The method of any one of clauses 15 to 19, wherein the subject is a human or an animal subject.

The invention claimed is:

1. An apheresis device, comprising: a monitoring device for measuring a level of cell free nucleosomes present in the blood of a subject, wherein the monitoring device comprises a solid phase with immobilized binding agents for binding cell free nucleosomes and wherein the monitoring device is configured to measure the level of cell free nucleosomes present in the blood of the subject in real-time.

2. An ex vivo organ perfusion device, comprising: a monitoring device for measuring a level of cell free nucleosomes present in a liquid perfusate, wherein the monitoring device comprises a solid phase with immobilized binding agents for binding cell free nucleosomes and wherein the monitoring device is configured to measure the level of cell free nucleosomes present in the blood of the subject in real-time.

3. The apheresis device of claim 1, further comprising one or more affinity matrices for removing one or more pathogenic substances from the blood of the subject.

4. The apheresis device of claim 1, wherein the binding agent binds to a feature of a core nucleosome that is common to all or most nucleosomes.

5. The apheresis device of claim 1, wherein the binding agent binds to an epigenetic feature of cell free nucleosomes.

6. The apheresis device of claim 5, wherein the epigenetic feature is selected from the group consisting of a histone isoform, a histone post translational modification, a particular nucleotide associated with a cell free nucleosome, and a protein adduct associated with a cell free nucleosome.

7. The apheresis device of claim 5, wherein the epigenetic feature is a histone post translation modification selected from citrullination.

8. The apheresis device of claim 5, wherein the epigenetic feature is histone isoform H3.1.

9. The apheresis device of claim 1, wherein the monitoring device is configured to measure the level of cell free nucleosomes by an immunochemical or biosensor method.

10. The apheresis device of claim 1, wherein the monitoring device comprises a panel of markers to be measured in the blood of the subject.

11. The apheresis device of claim 1, wherein the monitoring device additionally comprises binding agents to detect one or more interleukins present in the blood of the subject.

12. The apheresis device of claim 1, wherein the monitoring device included additionally comprises binding agents to detect one or more protein markers selected from the group consisting of C reactive protein (CRP), myeloperoxidase (MPO), D-Dimer and factor VII-activating protease (FSAP).

13. The apheresis device of claim 3, wherein the pathogenic substance is selected from the group consisting of cell free DNA (cfDNA), nucleosome-bound cfDNA, exosome-bound cfDNA and unbound cfDNA.

14. The apheresis device of claim 3, wherein the one or more affinity matrices are arranged in one or more affinity columns.

15. The apheresis device of claim 1, wherein the subject is a human or an animal subject.

16. A method of monitoring a subject during an apheresis procedure, comprising:

passing blood from a subject through an extracorporeal device that comprises a monitoring device for measuring a level of cell free nucleosomes present in blood, wherein the monitoring device comprises a solid phase with immobilized binding agents for binding cell free nucleosomes; and monitoring the level of cell free nucleosomes in the blood of the subject in real-time using the monitoring device of the extracorporeal device.

17. The method of claim 16, wherein a duration of the apheresis procedure is determined based upon the level of cell free nucleosomes in the blood of the subject measured using the monitoring device.

18. A method of treating a disease in a subject in need thereof, comprising:

passing blood from a subject through an extracorporeal device that comprises a monitoring device for measuring a level of cell free nucleosomes present in blood, wherein the monitoring device comprises a solid phase with immobilized binding agents for binding cell free nucleosomes; and monitoring the level of cell free nucleosomes in the blood of the subject in real-time using the monitoring device of the extracorporeal device.

\* \* \* \* \*